United States Patent
Cao et al.

(10) Patent No.: US 7,132,256 B2
(45) Date of Patent: Nov. 7, 2006

(54) METHODS FOR DETERMINING THE POTENCY, SPECIFICITY, AND TOXICITY OF MICROSOMAL PROSTAGLANDIN E2 SYNTHASE

(75) Inventors: Yang Cao, Bridgewater, NJ (US); Stephen Ayers, Logan Township, NJ (US); Jeffrey Sabol, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 11/165,779

(22) Filed: Jun. 24, 2005

(65) Prior Publication Data

US 2006/0024663 A1     Feb. 2, 2006

Related U.S. Application Data

(60) Provisional application No. 60/584,459, filed on Jun. 30, 2004.

(51) Int. Cl.
*C12Q 1/02*     (2006.01)
(52) U.S. Cl. ............................................... 435/29
(58) Field of Classification Search ................... None
See application file for complete search history.

(56) References Cited

OTHER PUBLICATIONS

Thoren et al, "Coordinate up- and down-regulation of glutathione-dependent prostaglandin E synthase and cyclooxygenase-2 in A549 cells (Inhibition by NS-398 and leukotriene C4)," (Eur. J. Biochem.) 2000 vol. 267, pp. 6428-6434.*

* cited by examiner

*Primary Examiner*—Christopher R. Tate
*Assistant Examiner*—Amanda P. Wood
(74) *Attorney, Agent, or Firm*—Karen I. Krupen

(57) ABSTRACT

Methods of determining the potency, specificity, and toxicity of microsomal prostaglandin E2 synthase inhibitors are provided that utilize one cell-based assay system.

12 Claims, 2 Drawing Sheets

METHODS FOR DETERMINING THE POTENCY, SPECIFICITY, AND TOXICITY OF MICROSOMAL PROSTAGLANDIN E2 SYNTHASE

FIELD OF THE INVENTION

The present invention relates to a novel and useful method for assaying compounds and agents for their ability to decrease or inhibit the activity of microsomal prostaglandin E2 synthase (mPGES). Specifically, the present invention relates to assays for measuring the potency, specificity and toxicity of mPGES inhibitors.

DESCRIPTION OF RELATED ART

Prostaglandins are a class of eiconisoids that play an important role in pain, fever and inflammation. They are synthesized from arachidonic acid, and possess a five-membered ring of carbon atoms that had formed part of the chain of arachidonic acid. Prostaglandins act locally, i.e., near the site of their synthesis. Prostaglandin E2, is particularly relevant in causing fever, pain and inflammation (Funk, C. *Science,* 294:1871–1875 (2001)).

PGE2 has been demonstrated to be an important pro-inflammatory and hyperalgesia-inducing lipid mediator. The synthesis of PGE2 is catalyzed by two classes of enzymes. The first class of enzymes, cyclooxygenases, generates prostaglandin H2 (PGH2) using an arachadonic acid precursor released from membrane phospholipids. Examples of cyclooxygenases include COX-1 and COX-2. The second class of enzymes, PGE2 synthases, produces PGE2 using a PGH2 precursor. Examples of PGE2 synthases include cytosolic PGE2 synthase (cPGES) and microsomal PGE2 synthase (mPGES) (Murakami, M et al, *Progress in Lipid Research* 43: 3–35, (2004)).

It has been shown that PGE2 is produced by two separate pathways. The first pathway produces PGE2 at a basal level. Constitutively produced PGES is expressed in the cytosol (cPGES) under basal conditions in a wide variety of mammalian cells. Under basal conditions, COX-1 stimulates the production of PGH2 from arachadonic acid, which in turn produces basal levels of PGE2 upon activation with cPGES. The second pathway produces PGE2 after induction by external stimulus such as cytokines and is localized to the microsomal compartment of the cell; hence is termed mPGES. Upon stimulation by a proinflammatory stimulus such as cytokines, COX-2 reacts with arachadonic acid to produce PGH2, which in turn induces mPGES to produce PGE2 from PGH2. (See FIG. 1). It is this second "inducible" pathway which is implicated in inflammation and hyperalgesia, whereas the first "constitutive" pathway has been shown to play little or none. (Murakami, M et al., *J. Biol. Chem.* 275: 32783–32792, (2000) and Tanioka et al, *J. Biol. Chem.* 275: 32775–32782 (2000)). Inhibitors of mPGES are known to be potentially useful for treating inflammation and pain.

An mPGES inhibitor may have undesirable qualities such as non-specificity and toxicity. For example, in addition to mPGES, there are other prostaglandin synthases, such as prostaglandin I2 synthase (PGIS), which catalyzes the formation of PGI2, a prostaglandin that causes vasodilation and inhibits platelet aggregation. A non-specific PGES inhibitor may inhibit these other prostaglandin synthases, resulting in undesirable side effects. Also, mPGES inhibitors may inhibit the basal production level of PGE2.

Since PGE2 plays an important role in fever, pain and inflammation, efforts have been made to create assays for compounds that may inhibit their production. In particular, techniques such as high pressure liquid chromatography (HPLC), enzyme-linked immunosorbent assays (ELISA), also known as enzyme immunoassays (EIA), or radioimmunoassays (RIA) have been used to quantify the production of PGE2 in order to determine a compound's or agent's ability to decrease or inhibit the production of PGE2.

In the past, assessments of potency, specificity and toxicity have been separated into different experiments. Moreover, specificity was more feasible in biochemical assays that in many cases could not mimic the real complex conditions in cells. It is desirable to design a cell based assay that measures potency, specificity and toxicity of mPGES inhibitors from the same experimental sample. Such a design would shorten the steps that usually require secondary screening and provide information that is more closely associated with the cell conditions in vivo.

BRIEF SUMMARY OF THE INVENTION

The present invention establishes a single cell-based assay to evaluate potency, specificity, and cytotoxicity simultaneously for mPGES inhibitors. mPGES inhibitors are potential therapeutic approaches for inflammation and pain. The assay design is suitable for use in any mammalian cell line in which PGE2 production has been shown to be induced by external stimuli. In the present invention, the mammalian cells are treated with one or more cytokines, such as TNFα and IL-1β. PGE2 is produced at such high levels that test inhibitor compounds may be evaluated by incubating the test compound with the cells and measuring the reduction of PGE2 in the supernatant. In addition to measuring the potency of a test compound, the present invention provides for specificity and cytotoxicity measurements all in the same cell-based assay system. This is designed by evaluating a second readout of the prostanoid 6-keto PGF1α, and by evaluating the effect of the test compound on the basal PGE2 production.

The above aspects and other aspects, features, and advantages of the present invention will be better understood from the following detailed description taken in conjunction with the accompanying figures.

DETAILED DESCRIPTION OF THE INVENTION.

The present invention relates to a cell-based assay for screening inhibitors of microsomal PGE2 synthase (mPGES). The assay evaluates potency, specificity and toxicity of test compound PGES inhibitors in living cells. The present invention allows for the identification of inhibitor compounds that may be used as oral drugs to treat pain, fever, Alzheimer's disease and many inflammatory diseases including but not limited to asthma, allergic rhinitis, arthritis, bowl inflammatory diseases and multiple sclerosis.

The present invention generally relates to a one cell based assay, which is used to measure potency, specificity and cytotoxicity for test mPGES inhibitor compounds, all in the same cell based assay. Measurements can be performed quickly and can be scaled up to test many different inhibitory compounds simultaneously.

There are no particular restrictions as to the inhibitor compound used. Examples are: a small molecular weight chemical molecules, libraries of synthetic low molecular compounds, purified proteins, expression products of gene libraries, synthetic peptide libraries, cell extracts and culture supernatants Any mammalian cell line may be used in the present invention as long as the mammalian cell line can be induced by one or more cytokines to express mPGES. The greater the induction of PGE2 upon cytokine stimulus, the larger the screening window available for measuring potency, specificity and cytotoxicity of test compounds. The preferred cell line is A549, a non-small lung cancer human epithelial cell line that is commercially available. However other mammalian cell lines may be substituted for A549 with ease such as human cell lines such as HEK 293, monkey cell lines such as COS cells and mouse cell lines such as J774.

Cell lines displaying high levels of PGE2 production upon stimulation by cytokine(s) are then used to measure the potency of compounds by incubating the test compound with the cells after stimulating with one or more external stimulus molecules. The external stimulus is selected from proinflammatory cytokines, growth factors and promoters.

Figure 1:
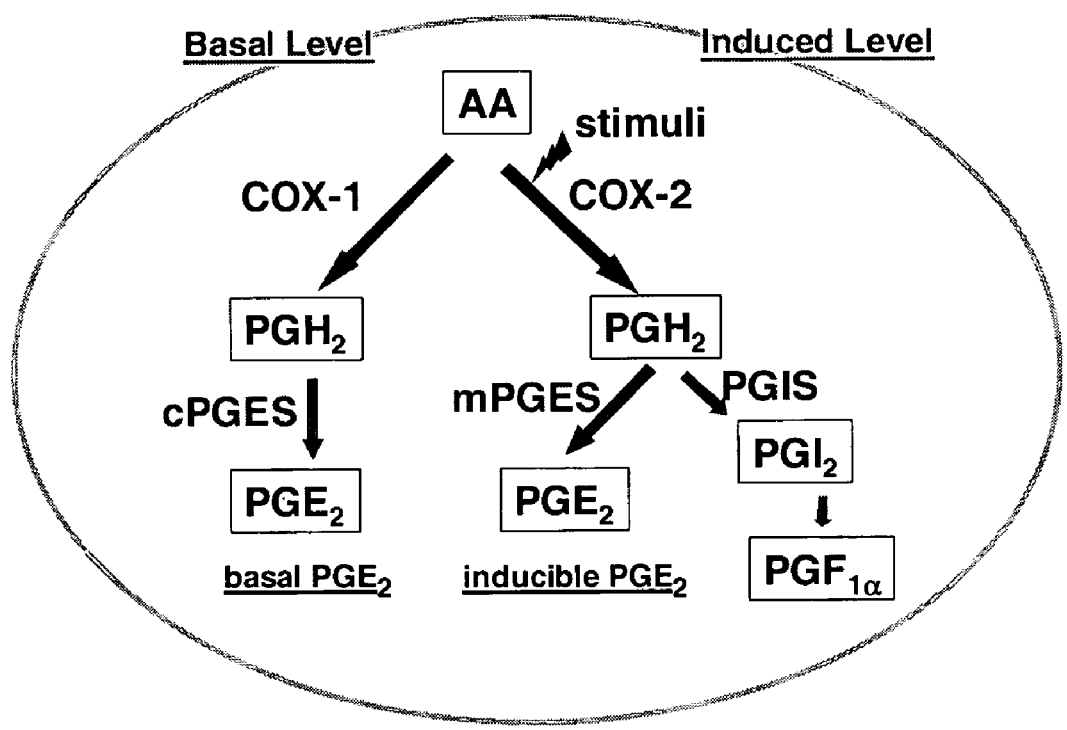
FIG. 1 is a schematic depiction of the arachidonic acid metabolic pathways. The abbreviations are as follows: arachidonic acid (AA), prostaglandin E2 ($PGE_2$), prostaglandin H2 ($PGH_2$), prostaglandin $I_2$ ($PGI_2$), 6-keto prostaglandin $F_{1\alpha}$, ($PGF_{1\alpha}$), prostaglandin $I_2$ synthase (PGIS), cytosolic PGE2 synthase (cPGES), microsomal PGE2 synthase (mPGES).

The concentration of PGE2 may be readily measured before and after stimulation with one or more cytokines, growth factors, promoters and the like by using an enzyme immunoassay specific for PGE2. The potency of the inhibitor compound is measured by the reduction of the PGE2 level in the supernatant after its addition. The present invention contemplates any stimulus compound either alone or in combination that is demonstrated to stimulate the inducible PGE2 pathway upon mixing with the chosen cell type. In a preferred embodiment, cytokines, growth factors or tumor promoters may be used either alone or together to stimulate PGE2 production in the chosen cell to induce PGE2 levels between 100 to 400 fold over basal levels. In a more preferred embodiment, A549 cells are stimulated with $TNF\alpha$ and IL-1$\beta$ to induce the COX-2 and mPGES coupled pathway for PGE2 production (see FIG. 1).

In addition to potency, the present invention incorporates the assessment of specificity and cytotoxicity of test compounds in the same cell-based assay system. This was designed by evaluating a second readout of the prostanoid production of 6-keto PGF1$\alpha$ and by evaluating the effect of test compounds on the basal PGE2 production, which is mediated by COX-1 and cPGES coupled pathway. (see FIG. 1).

Base inhibition measures the compound's effect on base-level production of PGE2, which is mediated by cPGES. Base level inhibition is determined by measuring PGE2 concentrations in non-induced cells in the absence and presence of the inhibitor compound.

Specific inhibition measures the compound's desired effect: namely, the production of PGE2 mediated by mPGES in an induced cell. Specific inhibition is measured by measuring PGE2 concentrations in induced cells in the absence and presence of the inhibitor compound. Thus, base and specific inhibition measurements are indicators of the cytotoxicity and specificity of the test compound.

In a preferred embodiment, A549 cells induced with both $TNF\alpha$ and IL1$\beta$ produces a synergistic 400-fold increase in the production of PGE2, which allows for a more precise measurement of inhibition levels (in terms of potency, specificity and toxicity) than previously contemplated.

Non-specific inhibition measures other effects that the test compound may have such as inhibiting enzymes other than mPGES. Non-specific inhibition is determined by measuring the compound's effect on the PGI2 pathway or other prostaglandin pathways, which catalyzes the production of PGI2, and ultimately 6-keto PGF1$\alpha$ (or other prostaglandins), from the same substrate as mPGES. In a preferred embodiment, concentration of 6-keto PGF1$\alpha$ is measured in the cell supernatant after induction in the absence and presence of the compound. If the compound is shown to inhibit production of 6-keto PGF1$\alpha$ as well as PGE2, then it may be inferred that the compound is not acting on mPGES alone, but also on some upstream element responsible for producing their common precursor such as PGH2.

Figure 2:
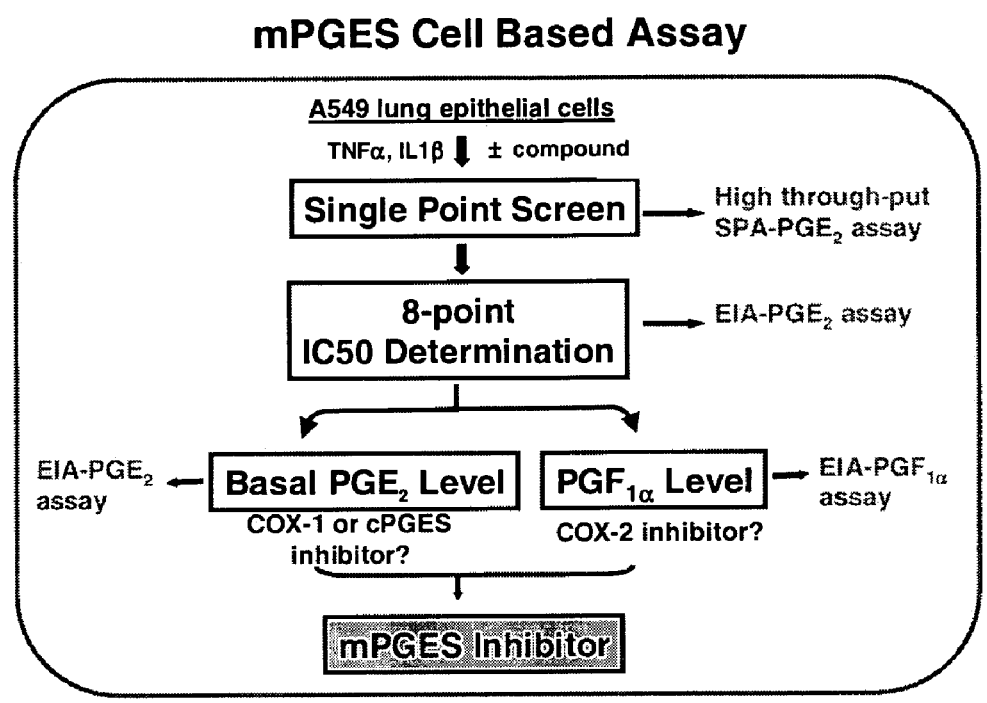
FIG. 2 is a representative screening system using both a single concentration (single point) and multiple concentrations (8 points in this example) of compound in the mPGES cell based assay. Test compounds may be quickly screened using high-throughput screening followed by IC50 measurements on positive hits using multiple concentrations of test compound.

The inhibition levels are determined, not just by taking measurements in the presence and absence of the inhibitor compound, but also at various concentrations thereof. By taking measurements at various inhibitor compound concentrations, it is possible to calculate certain properties, such as its IC50. An IC50 is defined as the concentration at which the compound produces 50% inhibition. (See FIG. 2, wherein 8 concentrations ("8-point") of the compound areprepared).

It is also understood that the assay of the present invention may also be conducted as a single point assay evaluating the inhibition of compound on PGE2 production using only one concentration of compound. Both single point screening and Ic 50 assays are amenable to high throughput screening. (See FIG. 2). High throughput screening systems are commercially available (see, e.g., Zymark Corp., Hopkington, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final reading of the samples in detector(s) appropriate for the assay. These configurable systems provide high throughput and rapid start up as well as a high degree of flexibility and customization. The manufacturers or such systems provide detailed protocols for the various high throughput assays. Methods of measuring concentration of PGE2 and 6-keto PGF1$\alpha$ are well known in the art. Examples include high pressure liquid chromatography (HPLC), gas chromatography mass spectrometry (GC-MS) enzyme-linked immunosorbent assay (ELISA), also known as enzyme immunoassay (EIA), radio-immunoassay (RIAs), fluorescence polarization (FP), and scintillation proximity assay (SPA).

The present invention is not limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All references cited herein are incorporated by reference in their entireties.

EXAMPLES

Example 1

Cell Treatment with Cytokines and Incubation with Test and Control Compounds

In this example, A549 cells were plated onto a 96 well flat-bottomed polystyrene plate at a density of 10^4 cells per well. The plate was then incubated overnight at 37° C.

The next day, a COX-2 inhibitor, NS398 (purchased from Cayman Chemical) was thawed and mixed well before use at a concentration of 1 mM. Aliquots of TNF-α and IL1-α (R & D Systems) were kept on ice until use. The test compound was thawed and placed on a table-top mixer at 500 rpm.

A set of sterile cluster tubes was arranged according to the following layout:

|  | Test Compound(s) |  | NS398 Control |  | Neg. Ctrl. | Pos. Ctrl. |
|---|---|---|---|---|---|---|
| 1st row | A (30 uM) | B (10 uM) | C (300 nM) | C (100 nM) | Media Only | C |
| 2nd row | C (3 uM) | C (1 uM) | C (30 nM) | C (10 nM) | Media Only | C |
| 3rd row | C (0.3 uM) | C (0.1 uM) | C (3 nM) | C (1 nM) |  |  |
| 4th row | C (0.03 uM) | C (0.01 uM) | C (0.3 nM) | C (0.1 nM) |  |  |

A, B, and C refer to media containing the TNF-α and IL1-β cytokines at three different concentrations of DMSO (Reagents A, B and C) as described below.

Reagent A contained culture cell media at a concentration of 5 ng/ml of TNF-α and 5 ng/ml of IL1-β without DMSO. Reagent B was created by adding DMSO to Reagent A to a concentration of 0.2% DMSO. Reagent C was created by adding DMSO to Reagent A to a concentration of 0.3% DMSO. 1 ml of culture media without cytokines was added to the negative control tubes. 200 μl of Reagent A was added to all tubes. 315 μl of Reagent A was added to the first column of cluster tubes. 315 μl of Reagent B was added to the second column of cluster tubes. 500 μl of Reagent C was added to the first row of NS398 control cluster tubes. 450 μl of Reagent C was added to the test compound cluster tubes in rows 2–4. 1 ml of Reagent C was added to positive control tubes. (See table above.)

To prepare a stock solution of the test compound, 2 μl of test compound from 10 mM stock was added to its corresponding tube (final dilution 1:100) and vortexed. Dilutions of the test compound were made as follows: 135 μl was taken from the stock solution and added to the 30 μM tube, and 45 μl was taken from the stock solution and added to the 10 μM tube. Serial dilutions are performed to generate concentrations of 30, 10, 3, 1, 0.3, 0.1, 0.03, 0.01, and 0.003 μM of compound.

To make a stock solution of control NS398, 2 μl of 1 mM NS398 was added to its corresponding tube (final dilution 1:100) and vortexed. Dilutions of NS398 were made as follows: 15 μl was removed from the stock solution and added to NS398 300 nM tube and 5 μl was removed from the stock solution and added to the NS398 100 nM tube. Serial dilutions are performed to generate concentrations of 300, 100, 30, 10, 3, 1, 0.3, and 0.1 nM of NS398.

After all dilutions were completed, the incubated cells were treated as follows. The media was removed from the cells and quickly replaced with the diluted compounds and controls. The 96-well plates were then incubated at 37° C. for 16 hours. The plates were centrifuged at 1000 rpm for 5 minutes. 80 μl of the supernatant from each well was collected for testing in either the enzyme immunoassay (EIA) or scintillation proximity assay (SPA) described in the following examples. Supernatants were stored at 4° C. for up to two hours or at −80° C. for up to three months.

For an alternative short-term assay, the A549 cells were treated with TNFα and IL1β first, and cells were incubated with cytokines at 37° C. for 16 hrs. The culture medium was replaced with HBSS buffer plus 0.1% BSA and the serial diluted compounds were then added for a preincubation of 30 minutes. Subsequently, 10 μM arachidonic acid was added and cell supernatant was collected after 30 minutes.

Example 2

Quantification of Prostaglandin Level: Enzyme Immunoassay

In this example, the concentration of PGE2 and 6-keto PGF1α were measured using an enzyme immunoassay (EIA). EIAs for measuring PGE2 and 6-keto PGF1α are available commercially. For example a PGE2 and 6-keto PGF1α EIA kits are available from Assay Designs. The PGE2 EIA employs a mouse monoclonal antibody specific for PGE2. The free PGE2 in solution competes with a known amount of PGE2 tracer to bind a limited amount of the anti-PGE2 antibody. The PGE2 tracer is a conjugate of PGE2 and acetylcholinesterase. The anti-PGE2 antibody is then fixed using a goat anti-mouse Ig antibody. The fixed antibody is then developed with Ellman's Reagent, which contains the substrate for acetylcholinesterase. The product produced by this reaction has a yellow color, and absorbs strongly at 412 nm. If there is a high concentration of PGE2, the PGE2 will outcompete the tracer and the resulting sample will have a weak absorbance at 412 nm. Conversely, if there is a low concentration of PGE2, the tracer will outcompete the PGE2 and the resulting sample will have a strong absorbance at 412 nm. In performing this assay, the absorbance at 412 nm was compared to a standard of absorbances at known concentrations of PGE2.

Similar assays can be performed for 6-keto PGF1α by substituting appropriate monoclonal antibodies and tracers. This assay may be easily converted to automated format by one skilled in the art by using a Zymark SciClone Deck, for example.

After the prostaglandin levels were determined in cells treated with 8 concentrations of test compounds, an IC50 of the compound was generated by conducting a semi-log plot of the prostaglandin level versus log scale of the compound concentration. This assay can also be conducted as a single point assay evaluating the inhibition of compound on PGE2 production using only one concentration of compound.

Example 3

Quantification of Prostaglandin Level: Scintillation Proximity Assay

In this example, the concentration of PGE2 in a cell suspension was measured using a scintillation proximity assay ("SPA"). As described in U.S. Pat. No. 4,568,649 for example, the SPA measures the concentration of a radiolabelled compound in a test sample.

An overnight mixture of antibody and beads was prepared by diluting an anti-PGE2 antibody (Cayman Chemical) into an assay buffer at 1:6.67 dilution. The assay buffer used was TBS with 0.05% Tween 20. SPA protein A beads were then added in an equal volume to the mixture. The mixture was mixed at 4° C. overnight.

A non-radioactive ("cold") PGE2 standard was diluted into 0.5% FBS media. Samples of the supernatant to be measured were similarly diluted.

A tracer was prepared such that 3-H PGE2 had a total radioactivity of 50 mCi in 500 µl total volume, and the reference average in 5 µl was $4.74 \times 10^5$ cpm.

The assay was performed by adding 20 µl of assay buffer to each well, 20 µl of cold standard or sample to the appropriate wells, 25 µl of tracer to all wells except for blank control wells, 130 µl of antibody/bead mixture to all wells except for non-specific binding (NSB) wells and 130 µl of appropriately diluted beads without antibody to NSB wells. The plate was shaken for two hours at room temperature. Radioactivity readings were taken using a Wallac 1450 Microbeta Trilux.

What is claimed is:

1. A method for screening for a compound that specifically inhibits mPGES in mammalian cells responsive to increased levels of PGE2 upon induction with an external stimuli comprising the steps of:
   i) contacting a mammalian cell with said compound,
   ii) stimulating said mammalian cell with an external stimuli,
   iii) measuring the level of PGE2 and 6-keto PGF1α in said mammalian cell, and
   iv) comparing the levels of PGE2 and 6-keto PGF1α in said mammalian cell to the levels of PGE2 and 6-keto PGF1α in a mammalian cell where no compound was added and yet another mammalian cell where no compound and no external stimuli was added, wherein potency is determined as the ratio of PGE2 levels in the presence and the absence of compound in the cells exposed to the external stimuli and wherein specificity and cytotoxicity is determined as the ratio of 6-keto PGF1α levels in the presence and absence of compound in the cells exposed to the external stimuli.

2. The method of claim 1 wherein said external stimuli is selected from one or more pro-inflammatory cytokines, growth factors and tumor promoters.

3. The method of claim 2 wherein said cytokines are TNFα and IL1β.

4. The method of claim 1 wherein said mammalian cell is selected from the group consisting of A549, HEK293, COS and J774.

5. The method of claim 4 wherein said mammalian cell is A549.

6. The method of claim 1 wherein said levels of PGE2 and 6-keto PGF1α are measured using HPLC, ELISA, GM-MS, EIA, RIA, FP or SPA.

7. A method for screening for a compound that specifically inhibits mPGES in mammalian cells responsive to increased levels of PGE2 upon induction with an external stimuli comprising the steps of:
   i) contacting a mammalian cell with said compound at two or more different concentrations of said compound,
   ii) stimulating said mammalian cell with an external stimuli,
   iii) measuring the level of PGE2 and 6-keto PGF1α in said mammalian cell, and
   iv) comparing the levels of PGE2 and 6-keto PGF1α in said mammalian cell to the levels of PGE2 and 6-keto PGF1α in a mammalian cell where no compound was added and calculate a percentage of control value, and subsequently an IC50 value based on two or more concentration points, and yet another mammalian cell where no compound and no external stimuli was added, wherein potency is determined as the IC50 of PGE2 in the presence and the absence of compound in said mammalian cells exposed to the external stimuli, and wherein specificity and cytotoxicity is determined as the IC50 of 6-keto PGF1α in the presence and absence of compound in said cells exposed to the external stimuli.

8. The method of claim 7 wherein said external stimuli is selected from one or more pro-inflammatory cytokines, growth factors and tumor promoters.

9. The method of claim 8 wherein said cytokines are TNFα and IL1β.

10. The method of claim 7 wherein said mammalian cell is selected from the group consisting of A549, HEK293, COS and J774.

11. The method of claim 7 wherein said mammalian cell is A549.

12. The method of claim 7 wherein said levels of PGE2 and 6-keto PGF1α are measured using HPLC, ELISA, GM-MS, EIA, RIA, FP or SPA.

* * * * *